United States Patent [19]

Davis, Jr.

[11] 4,432,757
[45] Feb. 21, 1984

[54] INDWELLING URETHRAL CATHETER

[76] Inventor: Richard C. Davis, Jr., 5828 - C Westower Dr., Richmond, Va. 23225

[21] Appl. No.: 366,963

[22] Filed: Apr. 9, 1982

Related U.S. Application Data

[62] Division of Ser. No. 148,340, May 9, 1980, Pat. No. 4,350,161.

[51] Int. Cl.³ ............................................. A61M 25/00
[52] U.S. Cl. ..................................... 604/99; 604/101; 604/256
[58] Field of Search ........................... 604/95–103, 604/256, 171, 280

[56] References Cited

U.S. PATENT DOCUMENTS

| | | | |
|---|---|---|---|
| 1,688,795 | 10/1928 | Aas . | |
| 2,638,093 | 5/1953 | Kulick | 128/133 |
| 3,087,493 | 4/1963 | Schossow | 604/96 X |
| 3,308,819 | 3/1967 | Arp | 604/164 |
| 3,331,371 | 7/1967 | Rocchi et al. | 128/DIG. 25 |
| 3,379,197 | 4/1968 | Hayes | 128/349 |
| 3,438,375 | 4/1969 | Ericson | 604/98 |
| 3,592,197 | 7/1971 | Cohen | 604/106 |
| 3,769,981 | 11/1973 | McWhorter | 604/96 |
| 3,797,478 | 3/1974 | Walsh et al. | 128/1 R |
| 3,805,794 | 4/1974 | Schlesinger | 128/349 |
| 3,811,450 | 5/1974 | Lord | 604/96 |
| 3,812,841 | 5/1974 | Isaacson | 128/1 R |
| 3,924,634 | 12/1975 | Taylor et al. | 604/100 |
| 3,938,529 | 2/1976 | Gibbons | 604/282 X |
| 4,026,298 | 5/1977 | Grauz | 128/DIG. 25 |

Primary Examiner—Dalton L. Truluck
Attorney, Agent, or Firm—Griffin, Branigan & Butler

[57] ABSTRACT

An indwelling urethral catheter (10) includes a flexible catheter drainage shaft (18) defining a drainage canal with a valve (32) mounted therein. The catheter is mounted in a urethral canal by means of a bladder-located Foley-type balloon (22) and an inflatable balloon lead shaft (24) which extends along the catheter drainage shaft. The valve (32) is normally biased to a closed position, but is actuatable to an open position by external hand manipulation of a penis in which the catheter is implanted. The catheter (10) also includes a discardable sleeve (12) which is severably attached to the distal end of the catheter (10), on the proximal side of the balloon (22). After insertion into the urethra, the balloon (22), and its lead shaft (24) are inflated through a "basketball" type contraction valve (44). Gentle traction is then applied axially to a catheter sleeve head (46) to sever the sleeve from the remainder of the catheter (10) so that it may be withdrawn from the urethra and discarded, leaving the remainder of the catheter (10) in a position whereby the most proximal end does not extend to the penile meatus.

5 Claims, 9 Drawing Figures

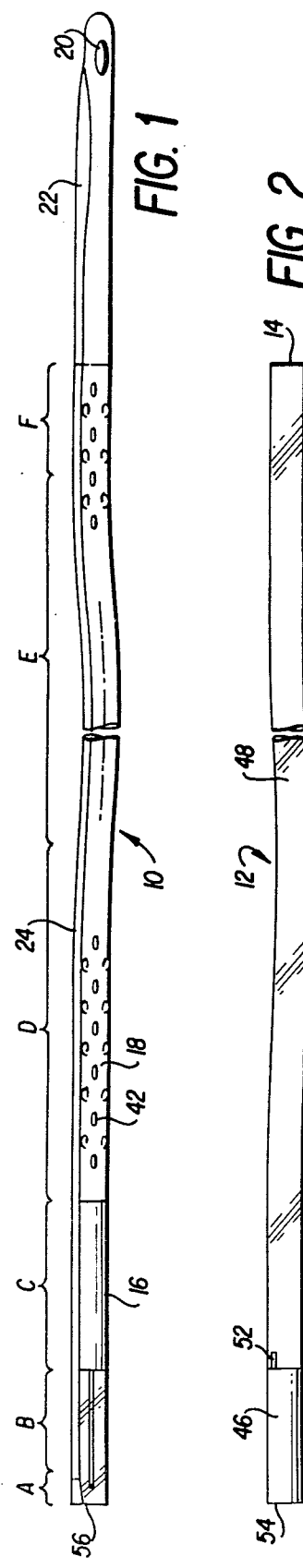
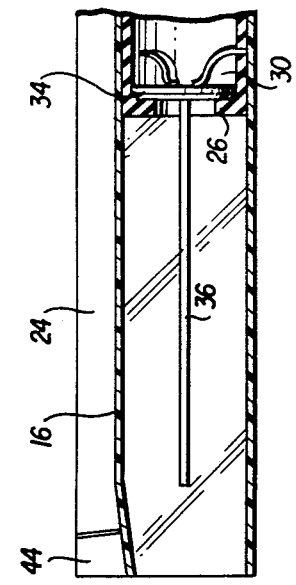
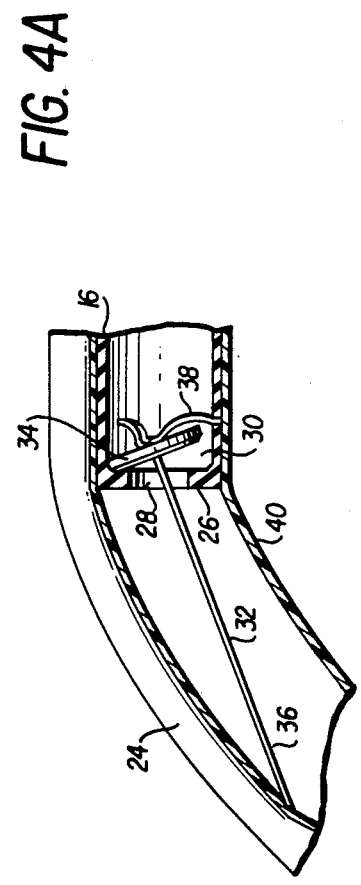
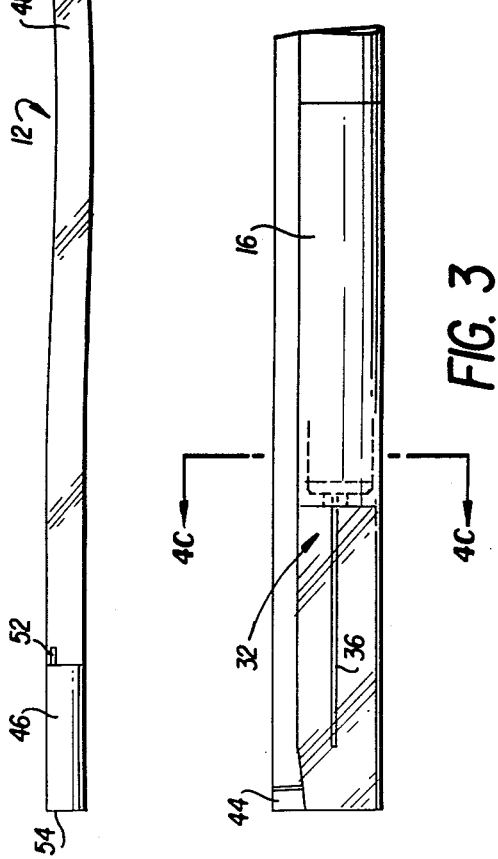
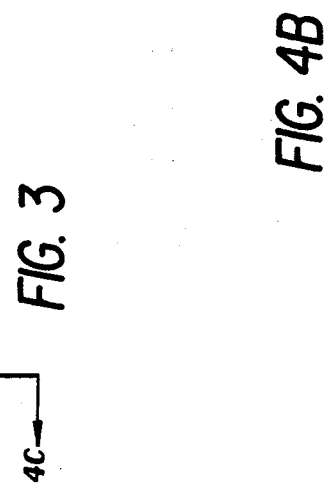

INDWELLING URETHRAL CATHETER

This is a division of application Ser. No. 148,340, filed May 9, 1980, now U.S. Pat. No. 4,350,161, issued Sept. 21, 1982.

BACKGROUND OF THE INVENTION

This invention relates broadly to the art of urethral drainage catheters, and in particularly to such catheters as they may be used by males.

Voluntary control over discharge of bladder contents is a serious and distressing problem for persons whose natural anatomy is no longer capable of completely controlling the outflow of urine from the bladder for such reasons as advanced age, surgery, disease, trauma, denervation, or other malformation of the natural lower urinary tract.

Traditional urethral balloon catheters of a well-known type comprise a flexible tube which extends from outside the body along the urethra and into the bladder. The tube comprises a main lumen for passage of urine and a much smaller lumen leading to an annular expandable balloon, which is adjacent the distal end of the catheter and which can be expanded within the bladder by pumping a fluid along the smaller lumen to thereby prevent accidental retraction of the catheter. In such a system, urine is continuously drained through the main lumen into a bag which is worn by the patient. Alternately, in some embodiments, the main lumen, or tube, is clamped outside of the patients body and the patient removes the clamp to drain urine. This known type of balloon catheter, while serving its purpose, suffers from a number of disadvantages.

Many of the disadvantages arising from a drainage lumen extending outside of a body relate to retrograde spread of extracorporeal bacteria backing up into the lumen. Also, such an externally-extending lumen allows reflux of air into the bladder. The spread of bacterial along the urethra, bladder, and ultimately to the kidneys, can, of course, cause infections which can be potentially fatal. It is not thought necessary to catalog all of the ramifications of this problem here. With regard to reflux of air into the bladder, the air, acting as a desiccant, can initiate the precipitation of urate and other normally soluable urine components in the bladder which create undesirable crystalline deposits therein.

Other problems which are produced by the above-described known type of balloon catheter stem from its interference with a patient's normal bodily functions, such as bathing, locomotion and sex. This, in turn, reduces a patient's body image and encourages a negative self-concept.

Further, a patient can accidentally snag the externally extending tube on something, or agitated, demented, disoriented, and/or otherwise confused patients can pull on the externally extending tube voluntarily. Such stresses on the tube can be disastrous for a patient, especially if traumatic extirpation ensues which can cause frank hematuria, stricture formation, infection, prostatitis, impotence, etc. Further, such situations can arouse feelings of frustration, animosity, and contempt in a patient or in medical staff members treating the patient.

U.S. Pat. No. 3,811,450 to Lord describes a catheter in which a drainage lumen extends only part way along the urethra, and therefore does not extend outside of a patient's body. However, in Lord's catheter there is a smaller tube for inflating a balloon and for removing the catheter extending out of the body. This smaller tube allows invasion of the body by bacteria and hampers normal body activity, such as sex. Also, Lord's catheter does not extend to the sphincter urethrae muscles, and requires those muscles to control urination. Thus, presumably, if those muscles are damaged. Lord's device cannot be used.

It is therefore an object of this invention to provide an indwelling urethral catheter which does not extend outside of the body but which is adequately held in position in the urethra. Also, it is an object of this invention to provide such a catheter which allows a patient to be continually continent while also controlling urination without necessarily requiring a functional lower urinary tract. Similarly, it is an object of this invention to provide structure for, and a method for, inserting such a catheter into a urethra.

Another difficulty with leading prior art urethral catheters is that external bags and tubes which must often be worn by patients using them, tend to emit an odor. In addition, often the patient cannot urinate at will as can most people, but must simply allow urine to drain into a bag. Both of these difficulties engender many of the psychological and physical problems which have already been set forth above. Therefore, it is another object of this invention to provide an indwelling urethral catheter which allows a patient to urinate at will so that urine is only expelled from the body under control of the patient with no external urine-contacting structures being necessary therefor.

SUMMARY

Accordong to principles of this invention, an indwelling urethral catheter intended primarily for males does not extend outside of a patient's body, but is positioned in the patient's penile urethra. The catheter includes a valve therein which is normally biased closed, but which can be selectively opened by a patient by externally manipulating his penis. The catheter has a Foley-type balloon to be inflated in the patient's bladder, but also includes an expandable balloon lead shaft extending along a catheter drainage shaft in the urethra for expansion therein. The catheter has spines thereon to help anchor the catheter drainage shaft in position in the urethra.

A sleeve surrounds the catheter drainage shaft and is frangibly attached thereto on the proximal side of the Foley-type balloon to be torn from the catheter and removed once the catheter is implanted in a patient. In this respect, the sleeve includes a head at the proximal end thereof which extends out of the penile meatus to provide a conduit for filling the balloon and its lead shaft with a fluid. The catheter-sleeve head includes a needle at its distal end which protrudes into a "basketball" type "contraction" valve situated in the balloon head shaft's proximal orifice.

BRIEF DESCRIPTION OF THE DRAWINGS

The foregoing and other objects, features and advantages of the invention will be apparent from the following more particular description of the preferred embodiment of the invention, as illustrated in the accompanying drawings in which reference characters refer to the same parts throughout the different views. The drawings are not necessarily to scale, emphasis instead has been placed upon illustrating principles of the invention in a clear manner.

FIG. 1 is a side view of a catheter of this invention as it is configured after it is mounted in a urethra, with the sleeve removed;

FIG. 2 is a side view of a catheter sleeve of this invention removed from the catheter of FIG. 1;

FIG. 3 is an enlarged isometric view of the proximal end of the catheter of FIG. 1;

FIGS. 4a and 4b are side sectional views of the proximal end of the catheter of FIG. 1 showing in some detail a valve mounted therein in respective closed and opened modes of operation;

DESCRIPTION OF THE PREFERRED EMBODIMENT

Figure 4C:
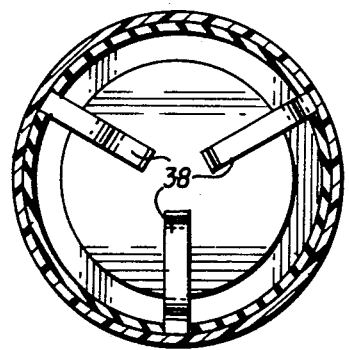
FIG. 4c is a sectional view taken on line 4c—4c in FIG. 3 showing the valve head of FIGS. 4a and 4b.
Figure 5:
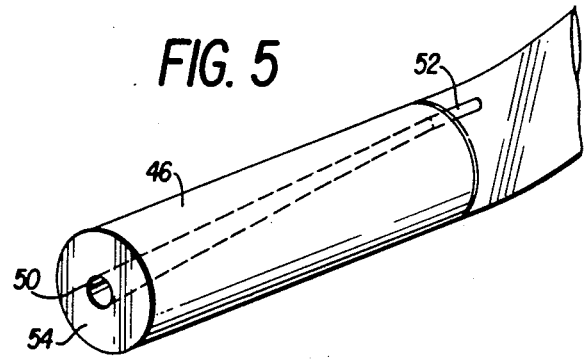
FIG. 5 is an enlarged, detailed, isometric view of the distal end of the catheter sleeve of FIG. 2.
Figure 6:
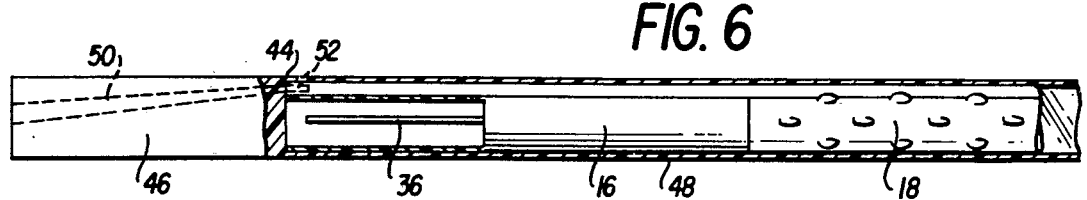
FIG. 6 is a side, partially cutaway view of the catheter of FIG. 1 with the sleeve of FIG. 2 mounted thereon.

A catheter assembly of this invention includes an indwelling urethral catheter 10 of FIG. 1 and a catheter sleeve 12 of FIG. 2. The catheter assembly is packaged and delivered with the catheter sleeve 12 being connected to the catheter 10 at a frangible zone 14 being shown in both FIGS. 1 and 2. This frangible attachment is made by a thin serrated membrane which serves to hold the sleeve 12 in place while the catheter unit is implanted, as is explained below.

Describing now in more detail the catheter 10, it comprises mainly a catheter/head valve assembly 16, a flexible catheter drainage shaft 18 with a multi-holed drainage orifice 20, and a balloon 22 with a partly expandable balloon lead shaft 24.

The catheter head/valve assembly 16 includes a rather rigid, plastic valve seat 26 (FIG. 4a) having a hole 28 therein. The hole 28 communicates with a passage 30 in the catheter head 16, and the passage 30 communicates with a main drainage canal (not shown) through the catheter drainage shaft 18. Mounted at the hole 28 is a special valve 32 which includes a head or flange, 34, and a stem, or lever, 36. The head, or flange, 34, is urged against the valve seat 26 by plastic spring clips 38 which are anchored to the relatively hard plastic member 40 forming the valve seat 26 at positions approximately 120 degrees apart. Thus, the special valve 32 is normally biased to a closed position against the valve seat 26. The catheter head 16 is covered by a resilient tubular member 40 which extends to the left of the valve seat 26, as viewed in FIGS. 4a and 4b, parallel to the valve stem 36, but being slightly longer than the valve stem 36 as can be seen in FIG. 4a. The valve head 34 is moved to an open position by the resilient tubular member 40 being flexed in any lateral direction such that it contacts the valve stem 36 to thereby pivot the head 34 as is viewed in FIG. 4b. Although depicted as being separate members, in another embodiment the tubular member 40 and the remainder of the casing of the catheter head 16 are integral one with the other.

Preferably, silastic compounds, or other state-of-the art biologically inert materials, are used in the construction of the catheter 10 and the catheter sleeve 12, including the resilient tubular member 40.

Turning next to the catheter drainage shaft 18, this element is similar to the drainage shafts of most indwelling urethral catheters, with the exception that it also includes protrusions, or spines 42, thereon for anchoring the drainage shaft in a urethra. A drainage canal extends from the multi-holed drainage orifice 20 through the passage (not shown) in the catheter drainage shaft 18 and out of the hole 28 in the valve seat 26, when the valve head 34 is in an open position.

The balloon 22 is a Foley-type balloon which surrounds the catheter drainage shaft 18 in a normal manner and which is located at a position proximal to the multi-holed drainage orifice 20. However, the balloon lead shaft 24 is somewhat different than normal balloon lead shafts. In this respect, the balloon lead shaft 24 is attached to the catheter drainage shaft 18 and to the catheter head 16 to extend parallel therealong. At its proximal end there is a "basketball" type "contraction" valve 44 for receiving a fluid-inserting needle. Such fluid is transmitted all along the expandable balloon lead shaft 24 through an inflation canal to the balloon 22. Through those portions of the balloon lead 24 designated as A, B, and C, in FIG. 1 the lead is non-expandable. However, beginning at the portion designated by letter D, it becomes expandable and becomes more and more compliant at points further distal, with the exception of area F, until becoming quite compliant at the balloon 22, which is the most compliant of all. Thus, the balloon lead 24 expands concurrently with the balloon 22, although to a graduated, lesser extent. The balloon lead shaft 24 is relatively non-compliant as it passes through the prostatic urethra, the portion labeled F on FIG. 1. This allows for the drainage of prostatic secretions into the urethral canal without tamponade. Furthermore, this structure allows for the unimpeded retrograde ejaculation of seminal fluid during sexual intercourse. Finally, this structure helps to exaggerate the regional anatomy using the prostatic urethra as a butress against which the dilated lead shaft in the bulbous urethra is juxtaposed.

The partially expandable balloon lead shaft serves three important functions as follows: firstly, expansion pressure of the lead holds the catheter 10, with spines 42, in place firmly, but gently, in the urethra. Secondly, by expanding, the lead denies normal ejaculation forcing it to retrograde into the bladder, but yet, since its expansion becomes more pronounced at distal locations, and the anchoring spines being only at the membranous urethra, the penis itself is freely manipulatable and is even free to expand to facilitate erections to thereby allow intercourse. Finally, by expanding, the lead also has the benefit of filling any potential space which could serve as a nidus of inflammation as well as gently seating the anchoring spines into the urethral mucosa. All of these benefits will be more clearly understood once the following description of the use of this catheter is fully explained below.

Turning next to the sleeve 12, this member is also constructed of various silastic compounds to have a relatively hard sleeve-head portion 46 and a flexible membrane portion 48.

With regard to the sleeve-head portion 46, this element serves mainly as a conduit for filling the balloon 22 and its partially expandable lead shaft 24 with a fluid after the catheter 10 is implanted. In this respect, the sleeve-head portion 46 has a passage 50 therethrough which communicates with, and extends through, a needle 52 protruding into the flexible-membrane portion 48. The needle 52 is positioned such that it can protrude into the contraction valve 44 of the balloon lead 24 so that fluid inserted into the passage 50 from a proximal end 54 is communicated into the balloon lead 24. The sleeve-head portion 46 is sufficiently long such that when the catheter 10, and an attached catheter sleeve 12 are first implanted in a urethra system, the proximal end 54 of the sleeve-head portion 46 extends outside of the penile meatus, while a proximal end 56 of the catheter 10 is located inside the penile urethra, spaced sufficiently behind the penile meatus to allow both proper closure of the orifice, as well as far enough back to avoid the colonization by normal surface flora which routinely inhabit the meatile antrum. In this attitude, the flexible-membrane portion 48 of the sleeve surrounds the catheter drainage shaft 18 and is severably joined thereto at 14.

Figure 7:
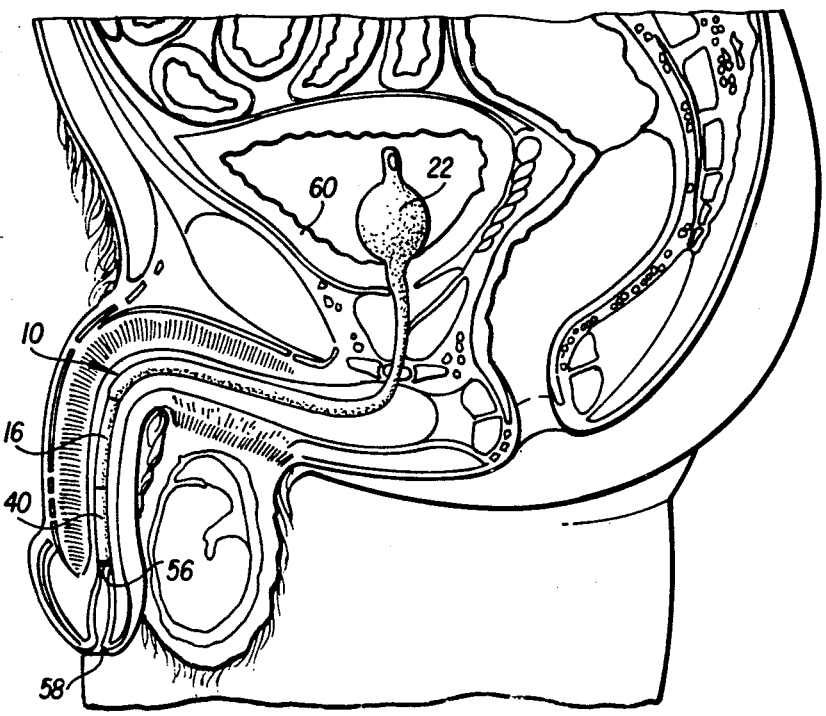
FIG. 7 is a sectional view of a penis and related organs having the catheter of FIG. 1 implanted therein.

Turning to operation of the indwelling urethral catheter assembly of this invention, firstly, the length of a patient's urethral tract is measured. This can be accomplished by implanting a conventional Foley-type catheter, placing a mark at the penile meatus when the penis is flacid, and withdrawing the conventional Foley-type catheter. A proper indwelling urethral catheter of this invention is then selected according to length. In this respect, the indwelling catheter of this invention, when it is operationally implanted in a patient should not extend outside of the tip of the penis 58, but rather should be spaced a short distance therefrom as is depicted in FIG. 7.

The catheter assembly is delivered to a surgeon or other operator in a sterile package, such as a long thin plastic bag which contains sterile lubricant. The catheter is then inserted through the penile meatus and the urethra to the bladder 60, with the balloon 22 being positioned inside the bladder 60. During this procedure, it should be remembered that the catheter sleeve 12 is still on the catheter 10 and is thereby protecting the urethral mucosa walls from the spines 42. Further, once the balloon 22 is in the bladder, the sleeve-head portion 46 extends outside of the penile meatus and thereby provides communication with the balloon lead 24 and the balloon 22 via the passage 50, the needle 52, and the contraction valve 44.

Once the catheter assembly is in place, with the balloon 22 in the bladder, a 10 cc syringe which is attached to and contiguous with the passage 50 at the proximal end 54 of the sleeve-head portion 46 is used to fill the balloon 22 and the balloon-lead shaft 24 with approximately 8 cc of sterile distilled water. Once the balloon and its lead 24 are inflated, the catheter is anchored against motion toward and away from the penile meatus and thereafter axial tension can be placed on the sleeve-head portion 46 of the catheter sleeve 12 without pulling the catheter 10 out of the urethra. As greater tension is placed on the catheter sleeve 12, the sleeve 12 finally is loosed from the catheter at the frangible zone 14 and the sleeve is pulled out of the urethra and discarded leaving the proximal end 56 of the catheter 10 spaced inwardly from the penile meatus 58. The operator then palpates the meatus to make sure that the catheter is in fact the correct size of the patient's urethral tract.

To empty the bladder the patient holds the penis between his thumb and index finger and flexes it, thereby moving the resilient tubular member 40 and the valve stem 36 laterally to move the valve head 34 to an open position as is depicted in FIG. 4b. Urine will flow until either the bladder is empty, or the penis is relaxed and the valve head 34 is returned to its normal closed position as shown in FIG. 4a.

To remove the catheter, one simply retracts the cleansed gland until the proximal end 56 of the catheter is exposed. A 10 cc syringe with an appropriate gauge needle is inserted into the contraction valve 44 and the sterile water is withdrawn. The withdrawal of this water creates negative pressure collapsing the balloon lead-shaft 24 and the anchoring spines 42 are loosened while the catheter is retracted with gentle pressure and discarded.

It can be appreciated by those skilled in the art that the indwelling urethral catheter of this invention is not only aesthetically superior to prior-art urethral catheters but also allows patients a much greater degree of comfort and freedom. In this respect, when the catheter is in place, a patient need not worry about inadvertently snagging the catheter or an associated urine bag or other collector. In fact, the patient need not wear a urine collector at all. Also, the patient can enjoy sexual intercourse in the normal manner.

This catheter is also particularly useful for agitated, demented, disoriented, and/or otherwise confused patients who are frustrated by foreign materials dangling from their bodies.

In addition, this invention offers many benefits with regard to fighting infections. In this respect, by being inwardly spaced from the penile meatus, the penis itself serves to keep out bacteria. Also, since the external skin of the catheter assembly, that is the catheter sleeve 12, is not removed until after the catheter assembly is implanted, there is less probability that the catheter itself introduces bacteria into the urethral tract.

While the invention has been particularly shown and described with reference to a preferred embodiment, it will be understood by those skilled in the art that various changes in form and detail may be made therein without departing from the spirit and scope of the invention.

The embodiment of the invention in which an exclusive property or privilege are claimed are defined as follows:

1. An indwelling urethral catheter comprising:
 a catheter drainage shaft means defining an enclosed drainage canal, for extending through most of a urethra to provide urinal drainage and having distal and proximal ends;
 said catheter drainage shaft means including an anchoring means for extending a substantial distance along said enclosed drainage canal for anchoring and holding said shaft in position in said urethra while not inhibiting said drainage canal from providing urinal drainage therethrough and for filling potential spaces which could serve as a nidus of inflamation along said urethra, said anchoring means having a substantially compliant wall for defining an inflation lumen which is separate from, but parallel to, said enclosed drainage canal along said drainage shaft means where said drainage shaft means is positioned in said urethra, downstream of the prostatic urethra;
 wherein said substantially compliant wall of said anchoring means is inflatable in a patient's urethra downstream of the patient's prostatic urethra by insertion of a fluid into said inflation lumen to fill spaces in the urethra and thereby anchor said catheter drainage shaft against retrograde movement in said urethra while allowing said enclosed drainage canal to provide urinal drainage;

and wherein said catheter being for use in male patients with the proximal end of the anchoring means not extending beyond the end of the penile meatus, said anchoring means including a valve means at the proximal end thereof for being held open by a fluid source means extending from outside the penis through the penile meatus to the valve means for allowing said inflatable member to be inflated by the fluid source means and for closing upon removal of the fluid source means through the penile meatus to leave said anchoring means inflated in said urethra.

2. An indwelling urethral catheter as in claim 1 wherein said catheter drainage shaft includes smooth protrusions thereon for protruding into walls of a patient's urethra.

3. An indwelling urethral catheter as in claim 1 wherein said valve means is a contraction valve.

4. An indwelling urethral catheter as in claim 1 wherein said anchoring means also includes a balloon for inflating in a patient's bladder.

5. An indwelling urethral catheter as in claim 4 wherein said balloon and said compliant wall are inflated through the same inflation lumen.

* * * * *